United States Patent
Foubert et al.

(10) Patent No.: US 8,338,169 B2
(45) Date of Patent: Dec. 25, 2012

(54) CELL/LIGAND MARKING SYSTEM, WHEREIN THE MARKER IS OF EPH TYPE, CELL MATERIAL COMPRISING SAID SYSTEM, METHOD FOR PREPARING SAME AND PROANGIOGENETIC USE

(75) Inventors: Philippe Foubert, Charenton le Pont (FR); Sophie Le Ricousse-Roussanne, Champigny-sur-Marne (FR); Jean-Sebastien Silvestre, Paris (FR)

(73) Assignees: Institut des Vaisseaux et du Sang (FR); Universite Paris 7-Denis Diderot (FR)

( * ) Notice: Subject to any disclaimer, the term of this patent is extended or adjusted under 35 U.S.C. 154(b) by 1076 days.

(21) Appl. No.: 11/996,862

(22) PCT Filed: Jul. 27, 2006

(86) PCT No.: PCT/FR2006/001837
§ 371 (c)(1),
(2), (4) Date: Jun. 20, 2008

(87) PCT Pub. No.: WO2007/012764
PCT Pub. Date: Feb. 1, 2007

(65) Prior Publication Data
US 2009/0123431 A1    May 14, 2009

(30) Foreign Application Priority Data
Jul. 27, 2005  (FR) ................................. 05 08029

(51) Int. Cl.
C12N 5/071  (2010.01)
C12N 5/078  (2010.01)
A61P 9/10  (2006.01)

(52) U.S. Cl. ....... 435/325; 435/372; 424/93.1; 514/13.3

(58) Field of Classification Search ........................ None
See application file for complete search history.

(56) References Cited

U.S. PATENT DOCUMENTS

| | | | |
|---|---|---|---|
| 6,579,683 B2 | 6/2003 | Wang et al. |
| 6,610,534 B2 | 8/2003 | Lian et al. |
| 6,864,227 B1 | 3/2005 | Wang et al. |
| 2003/0207447 A1 | 11/2003 | Wang et al. |
| 2004/0110150 A1 | 6/2004 | Koller et al. |
| 2005/0049194 A1 | 3/2005 | Frisen et al. |

FOREIGN PATENT DOCUMENTS

| | | |
|---|---|---|
| WO | WO 98/19712 | 5/1998 |
| WO | WO 00/31124 | 6/2000 |
| WO | WO 02/058538 | 8/2002 |
| WO | WO 02/079382 | 10/2002 |
| WO | WO 03/102144 | 12/2003 |
| WO | WO 2004/006846 | 1/2004 |
| WO | WO 2004/069264 | 8/2004 |
| WO | WO 2004/080418 | 9/2004 |

OTHER PUBLICATIONS

Kalka et al., Proc Natl Acad Sci U S A. Mar. 28, 2000;97(7):3422-3427.*
International Search Report and Written Opinion in French dated Apr. 2, 2007 issued in corresponding PCT Application No. PCT/FR2006/001837.
International Search Report in English dated Apr. 2, 2007 issued in corresponding PCT Application No. PCT/FR2006/001837.
Sophie Le Ricousse-Roussanne et al., "Ex vivo differentiated endothelial and smooth muscle cells from human cord blood progenitors home to the angiogenic tumor vasculature" Cardiovascular Research, vol. 62, No. 1, Apr. 1, 2004, pp. 176-184.
Hiromitsu Maekawa et al., "Ephrin-B2 induces migration of endothelial cells through the phosphatidylinositol-3 kinase pathway and promotes angiogenesis in adult vasculature." Arteriosclerosis Thrombosis and Vascular Biology, vol. 23, No. 11, Nov. 2003, pp. 2008-2014.
Kawamoto Atsuhiko et al., "Therapeutic potential of ex vivo expanded endothelial progenitor cells for myocardial ischemia" Circulation, vol. 103, (2001), pp. 634-637.
Donghun Shin et al., "Expression of ephrinB2 identifies a stable genetic difference between arterial and venous vascular smooth muscle as well as endothelial cells, and marks subsets of microvessels at sites of adult neovascularization" Developmental Biology, vol. 230, No. 2, Feb. 15, 2001, pp. 139-150.
Zhengyu Wang et al., "Ephrin receptor, EphB4, regulates ES cell differentiation of primitive mammalian hemangioblasts, blood, cardiomyocytes, and blood vessels." Blood, vol. 103, No. 1, Jan. 1, 2004, pp. 100-109.
Victor J. Dzau et al., "Therapeutic potential of endothelial progenitor cells in cardiovascular diseases." Hypertension (Baltimore), vol. 46, No. 1, Jul. 2005, pp. 7-18.
Aernout Luttun et al., "Vascular progenitors: From biology to treatment" Trends in Cardiovascular Medicine 2002 United States, vol. 12, No. 2, (2002), pp. 88-96.
Peter Carmeliet, "Angiogenesis in health and disease." Nature Medicine, vol. 9, No. 6, Jun. 2003, pp. 653-660.
Nicole K. Noren et al., "Interplay between EphB4 on tumor cells and vascular ephrin-B2 regulates tumor growth" Proceedings of the National Academy of Sciences of USA, National Academy of Science, Washington, DC, US, vol. 101, No. 15, Apr. 13, 2004, pp. 5583-5588.
Hal U. Wang et al., "Molecular distinction and angiogenic interaction between embryonic arteries and veins revealed by ephrin-B2 and its receptor Eph-B4" Cell, Cell Press, Cambridge, NA, US, vol. 93, No. 5, May 29, 1998, pp. 741-753.
E.B. Pasquale, *Curr. Opin. Cell Biol.*, 1997; 9(5):608.
Jean-Sébastien Silvestre, et al., "Regulation of Matrix Metalloproteinase Activity in Ischemic Tissue by Interleukin-10: Role in Ischemia-Induced Angiogenesis," Circulation Research, 2001, pp. 259-264.

* cited by examiner

*Primary Examiner* — Daniel C Gamett
(74) *Attorney, Agent, or Firm* — Ostrolenk Faber LLP (57) ABSTRACT

A cell/ligand specific marking system, the system being characterized in that it comprises: (a) an endothelial precursor cell (EPC) including a cell marker selected from among the group consisting of the Eph (in particular EphB4 or EphB1), and (b) a protein material of structure L-K, which consists of a ligand (L) specific of the marker and is associated or fused with a binding protein (K), the system being capable of providing a proangiogenetic cell material of structure EPC-Eph-L-K. The invention also concerns the cell material as product capable of stimulating angiogenesis, its preparation method and its therapeutic use, in particular with respect to vascular insufficiencies.

25 Claims, 4 Drawing Sheets

CELL/LIGAND MARKING SYSTEM, WHEREIN THE MARKER IS OF EPH TYPE, CELL MATERIAL COMPRISING SAID SYSTEM, METHOD FOR PREPARING SAME AND PROANGIOGENETIC USE

CROSS REFERENCE TO RELATED APPLICATION

The present application is a 35 U.S.C. §§371 national phase conversion of PCT/FR2006/001837, filed Jul. 27, 2006, which claims priority of French Patent Application No. 0508029, filed Jul. 27, 2005, the disclosure of which has been incorporated herein by reference. The PCT International Application was published in the French language.

FIELD OF THE INVENTION

The present invention relates to a novel technical solution using a system comprising a cell marker and a ligand specific for said marker, wherein said marker is selected from the group consisting of Ephs, in particular the EphB4 marker. It also relates to the cell material comprising this system and to the method for preparing it and its therapeutic use as a proangiogenic agent.

PRIOR ART

It is known that the members of the ephrin family and their Eph receptor tyrosine kinases, which were initially demonstrated in the nervous system for neurone guidance, are factors involved in angiogenesis. Many isoforms for Eph receptors and their ephrin ligands have been described with tissue expression specificities. In vertebrates, firstly, at least 16 Eph receptors are known, namely: 10 EphA receptors (EphA1 to EphA10) and 6 EphB receptors (EphB1 to EphB6) and, secondly, at least 9 ephrin ligands are known, namely: ephrin-A1 to ephrin-A6 and ephrin-B1 to ephrin-B3. Originally, the subdivision into two classes, EphA and EphB, was based on the homology of the sequence of their extracellular domain, but this subdivision also corresponds to the preferential binding of their ligands, the ephrin-A ligands being in general bound to the membrane by a glycosylphosphatidylinositol (GPI) and the ephrin-B ligands being transmembrane with an intracytoplasmic domain having a PDZ-binding domain.

Figure 1:
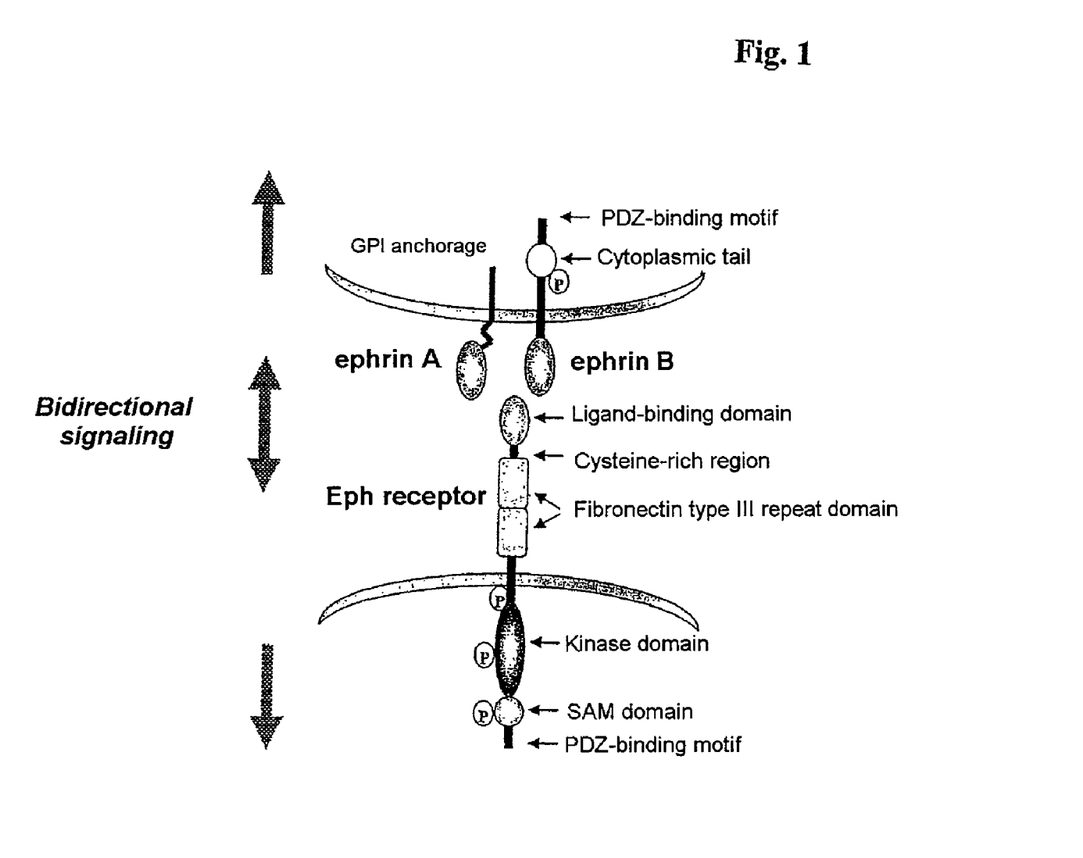
FIG. 1, presented in detail above, illustrates the prior state of knowledge and represents schematically the Eph receptor tyrosine kinases and their ligands of ephrin-A type or of ephrin-B type.

As represented in FIG. 1 hereinafter:
the Eph receptor comprises the extracellular domain, fibronectin type III repeats, a cysteine rich region and a specific ligand-binding domain; it also has an extension in the intracellular domain comprising a domain with tyrosine kinase activity, a sterile α motif (SAM) and a PDZ-binding motif;
the ephrin-A ligand is attached to the membrane via a GPI (GPI anchor); and
the ephrin-B transmembrane ligand has an intracellular extension comprising a cytoplasmic tail and a PDZ-binding motif.

With regard to the interaction between the Eph receptor tyrosine kinase (in particular EphB4) and its ligand (in particular ephrin-B2), a transmembrane protein, bidirectional signaling takes place, which comprises signaling induced by the Eph receptor in the cell expressing Eph on its surface (forward signaling) and reverse signaling induced by the ephrin ligand in the cell expressing ephrin at its surface. This bidirectional signaling plays a role in cell/cell contacts, migration and cell adhesion.

The specificity of arteriovenous expression of the EphB4/ephrin-B2 couple is known from the article by H. U. Wang et al., "Molecular distinction and angiogenic interaction between embryonic arteries and veins revealed by ephrin-B2 and its receptor EphB4", *Cell*, 1998; 93: 741-753, EphB4 being expressed only by the veins, and ephrin-B2 being expressed by the arteries.

EphB receptors and their ephrin-B ligands are expressed particularly during embryonic development. According to Z. Wang et al., "Ephrin receptor, EphB4, regulates ES cell differentiation of primitive mammalian hemangioblasts, blood, cardiomyocytes and blood vessels", *Blood*, 2004; 103: 100-109, EphB4 appears to be involved in the differentiation of mouse embryonic cells (ES) to endothelial cells.

It is also known that certain Eph receptors, in particular EphB4, are overexpressed in tumors. This observation suggests that these Eph receptors play a role in tumor progression. The article by N. K. Noren et al., "Interplay between EphB4 on tumor cells and vascular ephrin-B2 regulates tumor growth", *Proc. Natl. Acad. Sci. USA*, 101: 5583-5588, demonstrates that the activation of ephrin-B2 by EphB4 (reverse signaling) stimulates tumor growth.

On the other hand, what is observed with the prior literature is (i) an increase in the expression of ephrin-B2 during tumorigenesis and, secondarily, (ii) a concern, due to this increase, that ephrin-B2 would be capable of inducing tumors. This explains why several publications propose, on the one hand, using the detection of ephrin-B2 as a tumor marker or, on the other hand, inhibiting ephrin-B2; see, in particular, (i) WO 02/058538 A, which recommends detection of the ephrin-B2 ligand as a marker of the tumor vasculature and describes a technique for visualizing said tumor vasculature, (ii) US 2003/0207447 A, which proposes the use of an inhibitor of Eph, in particular EphB4, or of an inhibitor of ephrin, in particular ephrin-B2, for limiting angiogenesis by preventing the interaction between the receptor and the ligand, and (iii) U.S. Pat. No. 6,864,227 A and WO 03/102144 A, which recommend using either an anti-(Eph) antibody [in particular an anti-(EphB4) antibody] or an anti-(ephrin) antibody [in particular an anti-(ephrin-B2) antibody] for reducing or modulating angiogenesis.

Briefly, the published patent documents relating to the Eph/ephrin couple concern methods that relate in particular to:
ephrin-B signaling (reverse signaling) by proteins binding to the PDZ domain, see WO 02/079382 A and WO 00/031124;
modulation of the expression of ephrin-B2 or of EphB4, see in particular US 2004/0110150 A, WO 04/006846 A and WO 04/080418;
inhibition of the ephrin-B2/EphB4 interaction with a view to treating cancers and angiogenesis-related diseases, see in particular document WO 04/080418 A mentioned above and WO 04/069264 A; and
the use of ephrin-B2 as a marker for the tumor vasculature, see in particular document WO 02/058538 A mentioned above.

In addition, the article by Maekawa Hiromitsu et al. "Ephrin-B2 induces migration of endothelial cells through the phosphatidylinositol-3 kinase pathway and promotes angiogenesis in adult vasculature", *Arteriosclerosis thrombosis and vascular biology*, 2003, 23: 2008-2014, shows that the ephrin-B2 ligand, coupled to the Fc protein (i.e. the Fc fragment of an antibody), induces the migration of endothelial cells, HUVECs.

Finally, an adenovirus having the coding sequence of sphingosine kinase and a coding sequence of an angiogenic protein is known from U.S. Pat. No. 6,610,534 B. The objective of this patent is the expression of sphingosine kinase and of the angiogenic protein, which may be ephrin-B2, after local injection of said adenovirus. Moreover, a method for reducing the abnormal proliferation of hematopoietic stem cells, which comprises the administration by injection of a water-soluble inhibitor of ephrin-B2, is known from the publication US 2005/0049194 A.

OBJECTIVE OF THE INVENTION

According to the invention, it is proposed to provide a novel solution, neither described nor suggested in the above-mentioned prior art, to the technical problem of the stimulation of angiogenesis. More specifically, it is proposed here to provide a novel technical solution using a "cell marker/ligand specific for said marker" system which is applied to particular cells, namely endothelial precursor cells, for solving the problem of angiogenic stimulation. The objective pursued is that of improving previously known cell therapies by activating the cells before they are injected, so as to obtain greater effectiveness of revascularization processes, in particular post-ischemic revascularization.

SUBJECT OF THE INVENTION

The novel solution according to the invention uses a cell marker/ligand system wherein said marker is associated with an endothelial cell precursor cell. In this system, the marker is an Eph receptor and the Eph-specific ligand is an ephrin ligand.

According to a first aspect of the invention, a novel cell marker/specific ligand proangiogenic system is provided, said system, in which the cell marker is present on the outer membrane of the cell, being characterized in that it comprises:

(a) an endothelial precursor cell (EPC) comprising a cell marker selected from the group consisting of the Ephs, in particular EphB4 or EphB1, and (b) a protein material of structure:

L-K  (I)

which consists of a ligand (L) specific for said marker and is associated or fused with a binding protein (K), in particular an antibody Fc fragment, said system being capable of providing a cell material of structure:

EPC-Eph-L-K  (II)

which stimulates angiogenesis.

In other words, in order to stimulate angiogenesis, the EPC cells comprising the Eph marker are activated with the specific ligand L belonging to the ephrin family. The ligand L may also consist of a peptide fragment of an ephrin, for example of ephrin-B2, which then would have the same biological activity.

According to a second aspect of the invention, a cell material capable of stimulating angiogenesis is provided, said cell material being characterized in that it has the structure:

EPC-Eph-L-K  (II)

wherein said ligand L is associated with or fused with a binding protein K.

This cell material is capable (i) of being in the form of a substantially purified cell culture or in the form of a cell culture in combination with other precursor cells, in particular mononuclear cells, and (ii) of being, where appropriate, frozen.

According to a third aspect of the invention, a method for preparing said cell material is provided, said method being characterized in that it comprises the steps consisting in:

making use of EPCs expressing on their outer membrane a marker of the Eph family, in particular EphB4 or EphB1, and bringing said EPCs into contact, in vitro, with a protein material L-K wherein L is a ligand specific for said marker and K is a binding protein associated or fused with L.

A medicament that can be used for reconstituting damaged vessels, characterized in that it comprises, in combination with a physiologically acceptable excipient, a therapeutically acceptable amount of the cell material according to the invention, in particular as a proangiogenic active ingredient, is also recommended.

Finally, according to another aspect of the invention, a novel use of said cell material is provided, said use being characterized in that use is made of said cell material, as proangiogenic active ingredient, in combination with a physiologically acceptable excipient, for the preparation of a composition for therapeutic use in the treatment of vascular insufficiencies, in particular in the revascularization of ischemic cardiac, brain or peripheral tissues.

BRIEF DESCRIPTION OF THE DRAWINGS

In the attached drawings.

DETAILED DESCRIPTION OF THE INVENTION

The article by E. B. Pasquale, *Curr. Opin. Cell Biol.*, 1997; 9(5):608, in particular describes the specificities of the components of the Eph receptor/ephrin ligand system. For convenience, table I, given below and established according to this article (as indicated in U.S. Pat. No. 6,579,683 A), gives these specificities for certain couples, the ligands being placed in the second column by decreasing affinity with respect to their receptors reported in the first column.

In the cell marker/specific ligand system according to the invention, one can imagine that the two components of the couple can each be in the form of an amino acid sequence or, where appropriate, in the form of a nucleic acid sequence. It is, however, clearly rather preferable to have, at the start, an Eph receptor expressed on the EPC membrane in the form of an amino acid sequence. Similarly, the ephrin ligand will be very advantageously used in the form of an amino acid sequence or else of an ephrin peptide fragment. This is because it is in the form of amino acids that Eph and ephrin bind, the protein/protein interaction being necessary in order to observe the proangiogenic activity. Consequently, in the subsequent text, Eph and ephrin each intervene exclusively in the protein form of an amino acid sequence.

As Eph marker, an EphA or an EphB can be used here. However, it is preferred, according to the invention, for the Eph marker to rather be an EphB, since EphB markers are predominantly involved in angiogenesis, whereas (in the current state of knowledge) EphA markers appear to be mainly involved in the nervous system.

According to the invention, the EphB marker will advantageously be EphB4 or EphB1; among the EphB markers, EphB4 will be preferred to EphB1.

According to the invention, among the ephrin ligands, preference will be given to ephrin-B ligands, in particular ephrin-B2 or ephrin-B1. In addition, a variant of ephrin-B2, for example, which corresponds to a peptide fragment of ephrin-B2 having the same biological activity, may also be appropriate.

Consequently, in the system according to the invention, use will advantageously be made, firstly, of the EphB4 or EphB1 marker and, secondly, of the ephrin-B2 or ephrin-B1 ligand, the Eph/ephrin couple that is more particularly preferred according to the invention being EphB4/ephrin-B2.

In order for the ligand L to be able to activate EPC-Eph, it is important, in the majority of cases, for it to be associated with or fused with a binding protein K in the form of a protein material of structure:

$$L-K \qquad (I)$$

the recombinant ephrin-B2 protein being, to the applicant's knowledge, a substance capable of activating EPC-Eph alone without the introduction of said binding protein K.

Among the binding proteins K which are suitable according to the invention, mention may in particular be made of the numerous antibody Fc fragments (for example, those obtained by cleavage of antibodies with pepsin, papain or any other appropriate substance). For convenience, an Fc fragment readily available on the market as a by-product of the preparation of antibodies, such as Fab' and $F(ab)^2$, is recommended here.

As a variant, and given the above, said protein material L-K can be replaced with the recombinant, preferably human, ephrin-B2 protein.

The EPCs which are suitable according to the invention are cells which comprise an Eph cell marker (in particular an EphB, preferably EphB1 or better still EphB4) expressed at their outer membrane. Such EPC cells are obtained from mononuclear cells or cells expressing CD34 or CD133, which originate from the bone marrow, from peripheral blood or better still from umbilical cord blood.

The mononuclear cells are produced in the bone marrow, where they are found at a high concentration, pass into the blood stream and are found in cord blood and in peripheral blood. They constitute a material of choice, in the sense that, within their make-up, a considerable number of cells possess the genetic material required to (i) express the Eph marker (and more particularly the EphB4 marker) or (ii) include on their outer membrane said marker already expressed. The mononuclear cells that are preferred according to the invention are those which are $CD34^+$ or $CD133^+$, since, after differentiation, they provide a relatively large amount of EPCs which substantially express or include the EphB4 marker.

The concentration of EPCs produced by differentiation, which are contained in the population of mononuclear cells, varies according to the origin of the cells. Said concentration is more or less equivalent in the bone marrow and the umbilical cord blood. On the other hand, it is lower in peripheral blood.

The cell material according to the invention, which is represented by structure II above, in which the protein material L-K can be replaced with the recombinant ephrin-B2 protein, consists of one or more cells, each having on its outer membrane an Eph marker, in particular EphB4 or EphB1, bound to its specific ligand. As a variant, said cell material may consist of a culture containing several cells of structure II in combination, where appropriate, with other cells not activated by said protein material; such a culture may therefore be a cell mixture of activated EPCs, of nonactivated EPCs and of mononuclear cells.

According to a specific embodiment of the invention, said cell material is obtained by incubation
(a) of an endothelial precursor cell (EPC) comprising a cell marker selected from the group consisting of the Ephs, in particular EphB4 or EphB1, with
(b) a protein material of structure:

$$L-K \qquad (I)$$

which consists of a ligand (L) specific for said marker and is associated or fused with a binding protein (K), in particular an antibody Fc fragment, before being brought to its site of administration.

According to an advantageous embodiment, the incubation is carried out in vitro for a period of 10 to 60 minutes, in particular for 30 minutes, this incubation period being just before the administration of the cell material.

As a variant, said cell material may be in the form of a cell culture which is purified or which is a mixture of cells containing (i) EPC cells activated with L-K or the recombinant ephrin-B2 protein, and (ii) nonactivated precursors, for example mononuclear cells and/or EPCs, which are not activated with L-K or said recombinant ephrin-B2 protein. Furthermore, the cell material may be conserved in the frozen state.

The cell material that is preferred according to the invention, from the point of view of what was indicated above, is of structure II wherein said marker is EphB4 or EphB1, and wherein said ligand is ephrin-B2 or ephrin-B1.

According to a preferred embodiment, the method of the invention for preparing said cell material comprises the following steps:
(1°) making use of mononuclear cells originating from the bone marrow, peripheral blood or umbilical cord blood,
(2°) differentiating said cells of the preceding step in order to obtain EPCs having the Eph marker, and
(3°) activating the EPCs thus obtained in step (2°), in vitro, by binding of ephrin to Eph.

Said method comprises, where appropriate, an additional step between steps (1°) and (2°), i.e.:
(1a°) isolating the $CD34^+$ and/or $CD133^+$ mononuclear cells.

Step (1a°) implies a ternary process (1°)+(1a°)+(2°). However, the implementation of said step (1a°) increases the production costs compared with the binary process (1°)+(2°). In practice, since the nonactivated EPC cells serve to dilute the activated EPC cells in the cell medium containing them, without impairing their action, the binary process is at the current time manifestly more profitable than the ternary process.

According to the method of the invention, said ligand L is associated with or fused with a binding protein K in order to provide a cell material of structure:

$$EPC\text{-}Eph\text{-}L\text{-}K \qquad (II)$$

wherein advantageously said Eph marker is EphB4 or EphB1, and said ligand L is ephrin-B2 or ephrin-B1.

As medicament, the cell material according to the invention can be used for treating especially vascular insufficiencies, in particular in the revascularization of ischemic cardiac, brain or peripheral tissues.

The cell material according to the invention can be packaged in unit dose form, each dose containing the material of structure II. As a variant, it is possible to envisage a packaging according to which the components of said material II, i.e.

EPC-Eph and the protein material L-K, are not in contact; the incubation according to the reaction mechanism:

EPC-Eph+K-L→EPC-Eph-K-L being carried out before administration, in particular for the 10 to 60 minutes (preferably for the 20 to 30 minutes) that precede this administration.

In this case, a medicinal composition is recommended, which is characterized in that it comprises a therapeutically acceptable amount of the two components of the proangiogenic system according to the invention, which are packaged separately, each in a physiologically acceptable excipient, said two components being incubated before administration so as to give a cell material of structure II.

As indicated above, the cell material according to the invention is of use for regenerating vascular tissues which have been damaged in particular at the level of the heart or the brain or at the peripheral level. It is in particular suitable for the preparation of a composition for use in the treatment of arteritis, of coronary or cardiac vascular insufficiency and of cerebral vascular insufficiency. On an animal model, it has given good results, firstly, in the treatment of "critical" ischemia of the lower limbs and, secondly, in ensuring recovery making it possible to avoid amputation.

The cell material according to the invention can be administered to mammals, and in particular to humans, according to a method known per se. For example, said material can be (i) injected into or in the vicinity of the vascular lesion, (ii) injected into the blood via the IV route, or else (iii) brought to the site of the lesion by means of an appropriate vector. As a variant, it is possible to administer separately, by injection (in particular IV injection), firstly, the EPC-Eph cells and, secondly, the protein material bound to a vector known in the gene therapy field.

In adult humans, it is possible to administer, by IV injection, cells of structure II contained, where appropriate, in a cell mixture of nonactivated EPCs. Such a cell mixture may contain a total of approximately $10^5$ to $10^9$ cells per injection.

Other advantages and characteristics of the invention will be understood more clearly on reading the following examples of preparation and of pharmacological trials. Of course, this group of elements is not limiting but is given by way of illustration, the cell material used being: EPC-EphB4-ephrin-B2-Fc.

EXAMPLE 1

Obtaining EPC-EphB4

(A) Human umbilical cord blood samples are taken (from 30 to 50 ml each) and placed in sterile tubes containing an anticoagulant solution of sodium heparin. The umbilical cord blood mononuclear cells are isolated by density gradient centrifugation using Pancoll (1.077 g/ml, product sold by the company Dominique Dutscher S. A., Brumath, France). The mononuclear cells are then separated from the adherent cells by culturing on plastic dishes for 24 hours at 37° C. A cell mixture containing mononuclear cells expressing the EphB4 marker and mononuclear cells not expressing said marker is obtained.

(B) The cell mixture, obtained at the end of example 1(A), is placed in the wells of a 6-well plate coated with collagen type I (product sold by the company Sigma-Aldrich, Saint-Quentin, France) in a culture medium containing hVEGF for differentiation (as defined in the article by Le Ricousse-Roussanne S. et al., *Cardiovasc. Res.*, 2004; 62: 176-184). After culturing for 15 days, a cell mixture enriched in EPC-EphB4 is collected.

EXAMPLE 2

Obtaining EPC-EphB4

(A) Using the cell mixture obtained at the end of example 1(A), the CD34$^+$ cells are isolated and purified from the nonadherent cells by a standard immunomagnetic separation technique, in particular by means of the "CD34 isolation kit" (sold by the company Miltenyi Biotech, Paris, France), which comprises an anti-CD34 monoclonal antibody. The analysis of the cells thus obtained by flow cytometry and using an anti-CD34 monoclonal antibody (preferably different from the previous one), coupled to FITC, shows that 75% (±5.6%) of them have the CD34 marker.

(B) The cell mixture thus obtained, which contains $1.5 \times 10^6$ to $3.5 \times 10^6$ CD34$^+$ cells, can be placed in the wells of a 6-well plate coated with a matrix containing fibronectin, laminin, sodium heparin sulfate and collagen type I and IV (products sold by the company Sigma-Aldrich mentioned above) and in a culture medium containing hVEGF, bFGF and IGF1 (products sold by the company R&D Systems Inc., Oxford, United Kingdom). After culturing for 15 days, a cell mixture enriched in EPC-EphB4 is recovered.

EXAMPLE 3

Obtaining EPC-EphB4-ephrin-B2-Fc

After obtaining the cell mixture according to example 1(B), which contains EPC cells provided with the EphB4 marker, it is treated with 3 μg/ml of fusion protein ephrin-B2-Fc, EphB4-Fc or CD6-Fc (CD6-Fc being involved as the negative control for demonstrating the effect observed by the activation of the EPCs with ephrin-B2) for an incubation period of 30 minutes at 37° C. Each unbound fusion protein is discarded by rinsing (at least two rinses are carried out here).

Three cell mixtures are obtained, one of which contains the cell material according to the invention of structure EPC-EphB4-ephrin-B2-Fc, the second contains the cell material resulting from the activation of EPCs with the EphB4-Fc fusion protein, and the third contains the cell material resulting from the activation of EPCs with the CD6-Fc fusion protein.

EXAMPLE 4

Obtaining EPC-EphB4-ephrin-B2-Fc

The process is carried out as indicated in example 3 for obtaining cells of structure EPC-EphB4-ephrin-B2-Fc, with the difference that the starting cell mixture is that obtained at the end of example 2(B). The stated activated cells are obtained.

TRIAL PROTOCOL

At the time T=0, the right femoral artery of 7-week-old male nude mice (one batch of 6 animals per trial and per test product, including the PBS, nonactivated EPC and HUVEC controls) is ligatured so as to induce ischemia. At the time T=+4.5 h, the incubation according to example 3 is carried out so as to obtain the cell material of structure EPC-EphB4-ephrin-B2-Fc according to the invention and the other two cell materials for comparison. Next, at the time T=+5 h, each of the three cell mixtures obtained in example 3 is injected intravenously into the retroorbital sinus ($10^6$ cells/mouse). At the time T=+12 d, the mice are sacrificed and the gastrocnemius muscles of the limb rendered ischemic and of the nonischemic limb are removed. The following are determined:

the angiographic score;
the capillary density (i.e. the number of capillaries/mm$^2$); and
the cutaneous blood flow.

Figure 2:
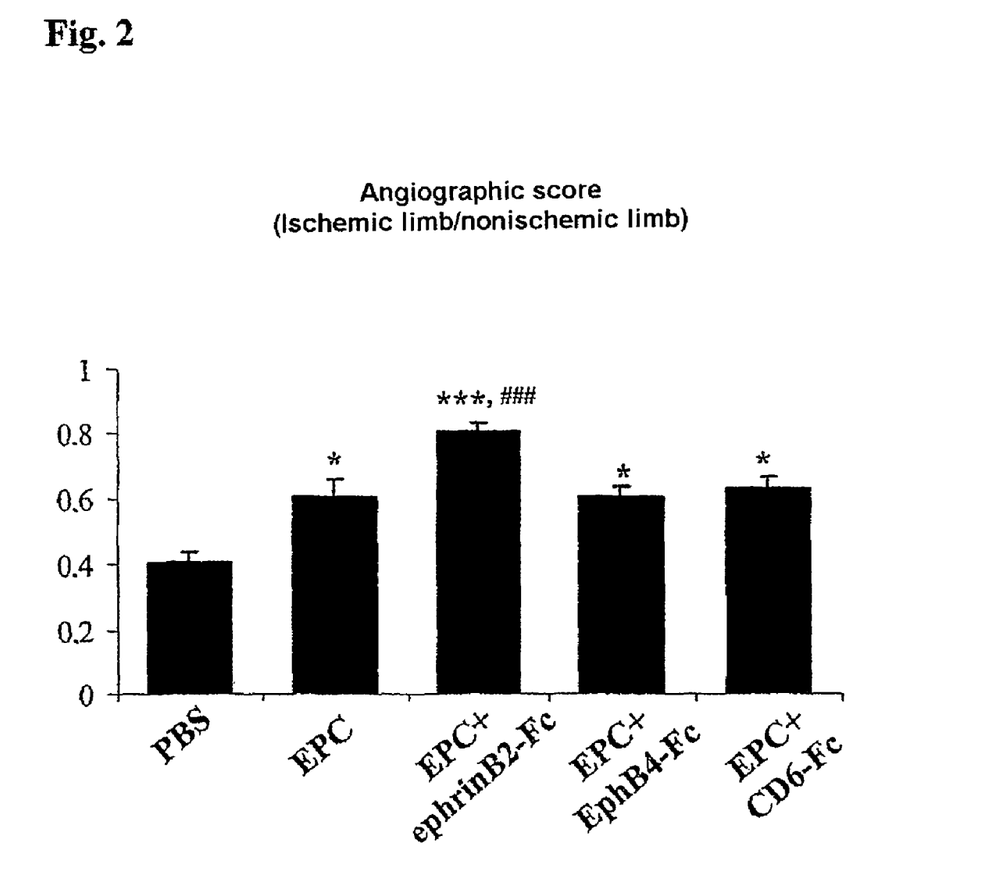
FIGS. 2 to 4 show graphically the proangiogenic properties, with regard to the tests which were carried out, of the cell material according to the invention.
Figure 3:
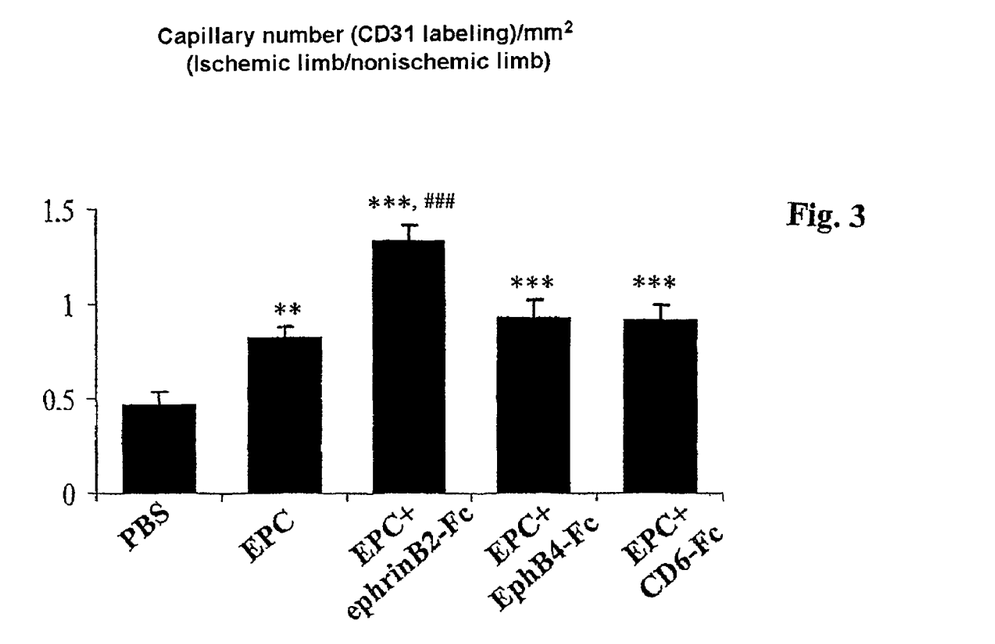
Figure 4:
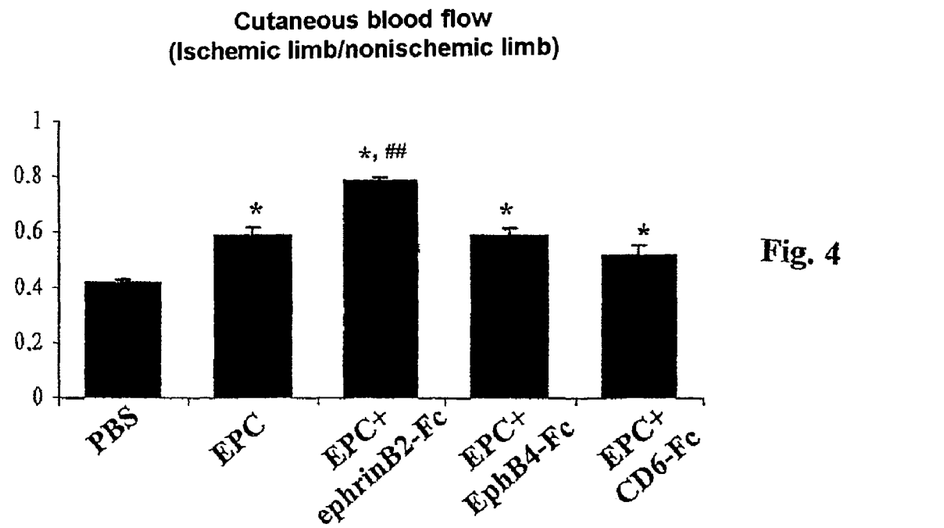

In FIGS. 2-4, the numerical values obtained are given in the form: mean±SEM.

TRIAL 1

Angiographic Score

The angiographic score (i.e. vessel density) was determined by microangiography. More specifically, the vessel density in the limb rendered ischemic, compared with the nonischemic limb, is measured by high-definition microangiography (see operating methods in the article by Silvestre J. S. et al., *Cir. Res.*, 2001; 89: 259-264). The results obtained, given in the form of a ratio (ischemic limb/nonischemic limb), are reported in the form of a graph in FIG. 2.

It is observed that the injection of the EPCs that are nonactivated or have been activated with the EphB4-Fc or CD6-Fc fusion protein slightly increase, and at comparable levels, the vessel density compared with the control group having received PBS. When the EPC cells are activated with the ephrin-B2-Fc fusion protein, it is noted that the increase in vessel density is 25.5% greater than that observed after injection of the nonactivated EPCs, i.e. a 1.34 times increase in the angiographic score.

TRIAL 2

Capillary Density (Number of Capillaries/mm$^2$)

The capillary density of the muscle rendered ischemic was studied by labeling sections of gastrocnemius muscle with an antibody directed against the CD31 marker, which is specific for endothelial cells, compared with sections of the same muscle of the nonischemic limb. The results obtained, presented in the form of a ratio (ischemic limb/nonischemic limb) are reported in the form of a graph in FIG. 3.

It is observed that the capillary density is 36.7% greater when the mice were treated by injection with the EPCs activated with the ephrin-B2-Fc fusion protein according to the invention, compared with the nonactivated EPCs, i.e. a 1.57 times increase in the capillary density.

TRIAL 3

Cutaneous Blood Flow

A quantitative evaluation of the blood flow, expressed by the ratio of the ischemic limb/nonischemic limb blood flow, was also carried out in order to verify that the variation in vessel number corresponds to a functional adaptation and therefore to a variation in the perfusion of the limb rendered ischemic. The results obtained are reported in the form of a graph in FIG. 4.

It is observed that the injection of the EPCs activated according to the invention with the ephrin-B2-Fc fusion protein increases the ratio of the blood flow in the limb rendered ischemic to the blood flow in the nonischemic limb by 1.37 times (27.1% increase).

EXAMPLE 5

Role of the EphB4 Marker

In this last example, the role of the EphB4 marker was demonstrated by virtue of cell preparations in which the EphB4 marker protein synthesis was inhibited.

For this, use was made of "interfering RNAs", or "siRNAs" capable in particular of specifically degrading the messenger RNAs encoding a given gene, and in particular in this case encoding the gene expressing the EphB4 marker. The specific action of these interfering RNAs is called transfection.

These cell preparations were administered to male nude mice according to a trial protocol similar to the trial protocol mentioned above.

In the first step, endothelial progenitor cells, or EPCs, are cultured to 80% confluence. Solutions of EphB4 siRNA, i.e. containing the interfering RNA, capable of inhibiting EphB4 marker protein synthesis are diluted in an M199 medium containing neither antibiotics nor serum, and incubated for five minutes at ambient temperature. Moreover, a solution of "control siRNAs" not corresponding to any particular gene is diluted under the same conditions. The latter diluted solution, which thus has no biological effect on the expression of the EphB4 marker, will simply make it possible to verify that the interfering RNAs have no activity of their own independently of their role of inhibitor.

Moreover, a transfection agent, Dharmafect2 (Dharmacon, Perbio) is prepared under the same conditions as the abovementioned solutions, and then mixed with these solutions, which are then subsequently incubated.

These incubated solutions are then brought into contact with the endothelial progenitor cells, EPCs, so as, in a first cell preparation, to cause inhibition of the EphB4 marker protein synthesis, and in a second cell preparation, where the expression of the gene encoding the EphB4 marker is not inhibited, to constitute a control.

These two cell preparations will, in turn, be respectively divided into two, and one of them will be stimulated with the ephrin-B2-Fc fusion protein before being injected intravenously into mice having been subjected to a ligature of the right femoral artery. In this way, four different cell preparations will be administered to the mice.

A summary of the results of this example 5 will be found in table I below.

TABLE I

| No. | PBS | 1 | 2 | 3 | 4 |
|---|---|---|---|---|---|
| Angiographic score | 100 | 161.5 +/− 10.7 | 218.8 +/− 12.8 | 153.5 +/− 2.9 | 158.9 +/− 12.5 |
| Blood flow | 100 | 144.5 +/− 4.5 | 193.5 +/− 4.7 | 151.1 +/− 8 | 138.5 +/− 14.1 |
| Capillary density | 100 | 147.4 +/− 10.7 | 201.7 +/− 12.8 | 142.6 +/− 11 | 140.8 +/− 11.3 |

1: EPCs transfected with the control siRNA and not stimulated before injection;
2: EPCs transfected with the control siRNA and stimulated with ephrin-B2-Fc before injection;
3: EPCs transfected with the EphB4 siRNA and not stimulated before injection;
4: EPCs transfected with the EphB4 siRNA and stimulated with ephrin-B2-Fc before injection.

It will be noted here again that the measurements of the angiographic score, of the blood flow and of the capillary density for the four cell preparations administered evolve substantially in parallel.

Moreover, it is immediately apparent that the result of the measurements for cell preparations no. 1, 3 and 4 are substantially identical, whereas the result for cell preparation no. 2 is greater by close to 40%.

Since the hypothesis is, of course, that the proangiogenic activity is promoted by the association of the EphB4 marker and the ephrin-B2-Fc protein material, it is noted, upon reading table I, by comparing the results of cell preparations no. 1 and 4, that the effect of the endothelial progenitor cells incorporating the "control siRNA" but not associated with the ephrin-B2-Fc protein material is substantially equivalent to the effect of the endothelial progenitor cells in which the expression of the EphB4 marker is inhibited but which are associated with the ephrin-B2-Fc protein material. Thus, it is shown that the interfering RNAs have no activity of their own independently of their role of inhibitor and that the endothelial progenitor cells, EPCs, expressing the EphB4 marker have no more activity than the endothelial progenitor cells, EPCs, not expressing the marker and which are associated with the ephrin-B2-Fc protein material.

Moreover, by comparing the results of the measurements of cell preparations no. 1 and 3, it is shown that the endothelial progenitor cells, EPCs, alone, expressing the EphB4 marker or not expressing it, have a comparable activity.

In addition, and this is the most important aspect, it is clearly shown, in view of the results of cell preparation no. 2 and in comparison with any of the other preparations, that the specific association of the EphB4 marker and of the ephrin-B2-Fc protein material exhibits considerable proangiogenic activity.

TABLE II

Specificities for some Eph/ephrin couples

| Eph receptors | Ephrin ligands (by decreasing affinity) |
|---|---|
| EphA1 | ephrin-A1 |
| EphA2 | ephrin-A3, -A1, -A5, -A4 |
| EphA3 | ephrin-A5, -A2, -A3, -A1 |
| EphA4 | ephrin-A5, -A1, -A3, -A2, -B2, -B3 |
| EphA5 | ephrin-A5, -A1, -A2, -A3, -A4 |
| EphA6 | ephrin-A2, -A1, -A3, -A4, -A5 |
| EphA7 | ephrin-A2, -A3, -A1 |
| EphA8 | ephrin-A5, -A3, -A2 |
| EphB1 | ephrin-B2, -B1, -A3 |
| EphB2 | ephrin-B1, -B2, -B3 |
| EphB3 | ephrin-B1, -B2, -B3 |
| EphB4 | ephrin-B2, -B1 |

The invention claimed is:

1. A cell material which stimulates angiogenesis, comprising:
(a) an endothelial precursor cell (EPC) comprising an EphB cell marker, and
(b) a protein material of structure:

$$L\text{-}K \quad (I)$$

which protein material consists of a ligand (L) specific for said marker that is associated or fused with a binding protein (K),
said cell material obtained by incubating said EPC with said protein material in vitro to provide a cell material of structure:

$$EPC\text{-}Eph\text{-}L\text{-}K \quad (II)$$

which is capable of stimulating angiogenesis.

2. The system as claimed in claim 1, wherein said marker is EphB4 or EphB1 and said ligand is ephrin-B2 or ephrin-B1.

3. The system as claimed in claim 1, wherein said ligand (L) is a peptide fragment of ephrin.

4. The system as claimed in claim 1, wherein the EPCs are obtained from mononuclear cells or from cells expressing CD34 or CD133, which originate from the bone marrow, from peripheral blood or from umbilical cord blood.

5. The system as claimed in claim 1, wherein the EPCs are obtained from peripheral blood or from umbilical cord blood.

6. The cell material of claim 1, said cell material being (i) in the form of a substantially purified cell culture or in the form of a cell culture in combination with other precursor cells, and (ii) which may be, where appropriate, frozen.

7. A medicament for reconstituting damaged vessels, wherein said medicament comprises a physiologically acceptable excipient and a therapeutically acceptable amount of a cell material as claimed in claim 6.

8. A method for the preparation of a composition for therapeutic treatment of vascular insufficiencies, wherein the method comprises combining a cell material as claimed in claim 1, for use as a proangiogenic active ingredient, and a physiologically acceptable excipient, to form said composition.

9. The method as claimed in claim 8, further comprising administering said composition to a subject in need of revascularization of at least one of ischemic cardiac, brain and peripheral tissues in said subject.

10. The system as claimed in claim 1, wherein said Eph is EphB4 or EphB1.

11. The system as claimed in claim 1, wherein said binding protein (K) is an antibody Fc fragment A.

12. The cell material as claimed in claim 1, wherein said endothelial precursor cells are mononuclear cells.

13. The cell material as claimed in claim 1, wherein said Eph is EphB4 or EphB 1.

14. The cell material as claimed in claim 1, wherein said binding protein (K) is an antibody Fc fragment.

15. The cell material as claimed in claim 1, wherein said ligand is a peptide fragment of ephrin.

16. A method for preparing a cell material which stimulates angiogenesis, wherein the method comprises the steps of:
providing EPCs expressing on their outer membrane an EphB marker, and
bringing said EPCs into contact, in vitro, with a protein material L-K, wherein L is a ligand specific for said marker and K is a binding protein associated or fused with L.

17. The method as claimed in claim 16, wherein said marker is EphB4 or EphB1.

18. The method as claimed in claim 16, comprising the following additional steps:
(1°) providing mononuclear cells originating from the bone marrow, peripheral blood or umbilical cord blood,
(2°) differentiating said cells of the preceding step (1°) in order to obtain EPCs having the Eph marker, and
(3°) activating the EPCs thus obtained in step (2°), in vitro, by binding of ephrin to Eph.

19. The method as claimed in claim 18, wherein the method further comprises, between steps (1°) and (2°), an additional step of:
(1a°) isolating $CD34^+$ and/or $CD133^+$ mononuclear cells, and wherein said step (2°) comprises differentiating the cells isolated in step (1a°).

20. The method as claimed in claim 18, wherein in step (1°), the mononuclear cells originate from peripheral blood or from umbilical cord blood.

21. The method as claimed in claim 16, where K is an antibody Fc fragment.

22. The method as claimed in claim 16, wherein the marker is EphB4 or EphB1 and said ligand L is ephrin-B2 or ephrin-B1.

23. The method as claimed in claim 16, wherein said ligand is a peptide fragment of ephrin.

24. A medicinal composition for reconstituting damaged vessels, wherein said composition comprises a therapeutically acceptable amount of the cell material of structure: EPC-EPH-L-K (II), wherein said cell material is formed by incubating a first component, (a) an endothelial precursor cell (EPC) comprising an EphB marker with a second component, (b) a protein material of structure L-K, which protein material consists of a ligand (L) specific for said marker that is associated or fused with a binding protein (K) and wherein, before said incubation, components (a) and said (b) are each packaged separately in a physiologically acceptable excipient.

25. A cell marker/specific ligand proangiogenic system, said system, in which the cell marker is present on the outer membrane of the cell, comprising:
 (a) an endothelial precursor cell (EPC) comprising an EphB marker, and
 (b) a recombinant ephrin-B2 protein,
 said system being formed in vitro and providing a cell material of structure: EPC-Eph-recombinant ephrin-B2 protein, which is capable of stimulating angiogenesis.

\* \* \* \* \*